(12) United States Patent
Warnock et al.

(10) Patent No.: US 11,277,947 B2
(45) Date of Patent: Mar. 15, 2022

(54) ELECTROMAGNETIC AND RADIATION SHIELDING SYSTEM

(71) Applicant: New England Lead Burning Company, Inc., Burlington, MA (US)

(72) Inventors: Seth Warnock, Chester, NY (US); Rodney Gebert, Hazlehurst, WI (US); Frank Leban, Orland Park, IL (US)

(73) Assignee: NEW ENGLAND LEAD BURNING COMPANY, INC., Burlington, MA (US)

( * ) Notice: Subject to any disclaimer, the term of this patent is extended or adjusted under 35 U.S.C. 154(b) by 0 days.

(21) Appl. No.: 16/801,603

(22) Filed: Feb. 26, 2020

(65) Prior Publication Data

US 2020/0275586 A1 Aug. 27, 2020

Related U.S. Application Data

(60) Provisional application No. 62/810,567, filed on Feb. 26, 2019.

(51) Int. Cl.
*H05K 9/00* (2006.01)
*A61N 5/10* (2006.01)

(52) U.S. Cl.
CPC ............ *H05K 9/0003* (2013.01); *A61N 5/10* (2013.01); *H05K 9/0015* (2013.01); *A61N 2005/1094* (2013.01)

(58) Field of Classification Search
CPC .................................................. H05K 9/0003
See application file for complete search history.

(56) References Cited

U.S. PATENT DOCUMENTS

| | | | |
|---|---|---|---|
| 6,992,246 B2 | 1/2006 | Christou | |
| 2007/0007037 A1* | 1/2007 | Diaferia | H05K 9/0015 174/382 |
| 2010/0094117 A1* | 4/2010 | Kruemmel | H05K 9/0001 600/409 |
| 2018/0258659 A1 | 9/2018 | LeBlanc et al. | |

* cited by examiner

*Primary Examiner* — Hung V Ngo
(74) *Attorney, Agent, or Firm* — Kriegsman & Kriegsman

(57) ABSTRACT

An electromagnetic and radiation shielding system includes an enclosure shaped to define a room interior which is accessible through a single passageway, and a door assembly for selectively enclosing the passageway. The door assembly includes a frame mounted within the passageway in conductive contact with a metal skin incorporated into the enclosure, a door with a conductive rear face which is adapted to selectively enclose the passageway, and a seal for selectively establishing continuous, peripheral contact between the frame and the rear face of the door when the door is disposed in its closed position. In this manner, the door assembly cooperates with the enclosure to form an electromagnetic barrier around the room interior in all directions. Additionally, both the enclosure and the door are constructed with a layer of radiation-shielding material to form a radiation barrier around the room interior in all directions.

12 Claims, 11 Drawing Sheets

ELECTROMAGNETIC AND RADIATION SHIELDING SYSTEM

CROSS-REFERENCE TO RELATED APPLICATIONS

The present application claims the benefit under 35 U.S.C. 119(e) of U.S. Provisional Patent Application No. 62/810,567, which was filed on Feb. 26, 2019 in the names of Seth Warnock et al., the disclosure of which is incorporated herein by reference.

FIELD OF THE INVENTION

The present invention relates generally to medical diagnostic and/or treatment equipment which produces high-energy electromagnetic radiation and, more particularly, to shielded enclosures which are designed to house such equipment.

BACKGROUND OF THE INVENTION

In the healthcare industry, various types of medical devices are designed to emit high-energy electromagnetic radiation in order to diagnose and/or treat patients. For example, diagnostic imaging tools, such as magnetic resonance imaging (MRI) scanners, computed tomography (CT) scanners and X-ray machines, use electromagnetic radiation (e.g., radio waves, X-rays, and the like) to generate images of the human body for diagnostic purposes. Additionally, radiation therapy equipment, such as linear accelerators (LINACs), use high-energy electromagnetic radiation (e.g., X-rays, gamma rays, and the like) to shrink and/or destroy cancerous cells without impinging healthy cells.

Healthcare facilities are typically provided with shielded rooms, or enclosures, which are specifically designed to house such equipment. In this capacity, shielded rooms form a barrier which prevents the penetration of certain types of electromagnetic energy therethrough.

As an example, a radiation shielding enclosure, also known in the art simply as a radiation bunker, is a room which is uniquely designed to prevent the escape of radiation produced by radiation therapy equipment contained therein. In a radiation bunker, a radiation shielding material, such as concrete, lead, steel or a combination thereof, is incorporated into each of the walls, ceiling and flooring of the room so as to fully enclose the room interior. In this manner, the radiation shielding material prevents the escape of any potentially-harmful radiation produced by the radiation therapy equipment into the ambient environment. An illustrative radiation bunker is shown in U.S. Patent Application No. 2018/0258659 to R. L. LeBlanc et al., the disclosure of which is incorporated herein by reference.

As another example, an electromagnetic shielded enclosure, also commonly referred to in the art as a radio frequency (RF) shielded enclosure or electromagnetic interference (EMI) shielded enclosure, is a room which is specifically designed to attenuate RF energy. Typically, in an RF shielded enclosure, an electrically conductive skin (e.g., a metal sheet, meshing, or screen) is incorporated into each of the walls, ceiling and flooring of the room so as to fully enclose the room interior. In this manner, the conductive skin forms a cage-like barrier which blocks the transmission of any electromagnetic energy that may potentially create RF interference with equipment located inside and/or outside the room.

In all forms of shielded enclosures, the passageway, or doorway, serves as the primary means of disruption to the energy shielding barrier. Accordingly, the particular means for enclosing the passageway is of critical importance in ensuring adequate shielding properties.

In radiation bunkers, an enlarged, slab-like door constructed of a suitable radiation shielding material, such as concrete and/or steel, is commonly utilized to selectively enclose the passageway in an overlapping fashion. As such, a fully-enclosed radiation barrier surrounds the room interior in all directions and thereby prevents emission of radiation into the outside environment.

In RF shielded enclosures, an electrically-conductive door is commonly utilized to selectively enclose the passageway. Additionally, a resilient conductive seal is established between the remainder of the shielded room and the peripheral edge of the conductive door. In this manner, a fully-enclosed RF barrier surrounds the room interior in all directions and thereby blocks the transmission of RF energy therethrough. An example of a conductive seal disposed about the periphery of a metal door in order to create an EMI shielded room is shown in U.S. Pat. No. 6,992,246 to C. Christou, the disclosure of which is incorporated herein by reference.

Increasingly, shielded rooms are required to provide both radiation and RF shielding capabilities. In fact, hybrid diagnostic and treatment equipment, such as a hybrid MRI scanner and linear accelerator, or MR-Linac, have grown into prominence in the field. Through a single medical procedure, hybrid equipment of this type is able to engage in diagnostic imaging to identify the presence of any cancerous cells and, in turn, focus high-energy radiation onto any identified cells with great precision as part of a cancer treatment plan.

Commonly, shielded rooms with both EMI and radiation shielding capabilities are designed as two separate enclosures, with one typically nested inside the other. For instance, an EMI shielded enclosure, with a first door assembly, typically defines the immediate periphery of the room interior. A radiation bunker, with its own separate door assembly, is then constructed around the EMI shielded enclosure to additionally provide the room with radiation shielding capabilities.

The construction of a single EMI and radiation shielded room with two independent door assemblies has been found to introduce a number of notable shortcomings.

As a first shortcoming, an EMI and radiation shielded room of the type as described above is operationally inefficient. More specifically, the time required to open and close two independent doors reduces the rate that patients and staff can routinely enter into and exit the room. As a result, patient throughput is significantly compromised.

As a second shortcoming, an EMI and radiation shielded room of the type as described above is relatively complex in construction. Notably, the inclusion of two independently operating doors substantially increases overall manufacturing and installation costs.

As a third shortcoming, an EMI and radiation shielded room of the type as described above is spatially inefficient due to the inclusion of two separate nested enclosures. As a result, shielded rooms of this type typically require either a greater physical footprint or a reduction in the size of the room interior.

SUMMARY OF THE INVENTION

It is an object of the present invention to provide a new and improved electromagnetic and radiation shielding system.

It is another object of the present invention to provide an electromagnetic and radiation shielding system which includes a single, room-like enclosure that is designed with both an electromagnetic shield for attenuating radio frequency energy and a radiation shield for preventing the escape of high-energy radiation produced by radiation therapy equipment.

It is yet another object of the present invention to provide a system as described above wherein access to the interior of the enclosure is limited to a single passageway.

It is still another object of the present invention to provide a system as described above which utilizes a single door to selectively enclose the passageway.

It is yet still another object of the present invention to provide a system as described above wherein the single door cooperates with the electromagnetic shield in the enclosure to form a complete electromagnetic barrier around the room interior in all directions.

It is another object of the present invention to provide a system as described above wherein the single door cooperates with the radiation shield in the enclosure to form a complete radiation barrier around the room interior in all directions.

It is yet another object of the present invention to provide a system as described above which is simple in construction, quick and easy to operate, and inexpensive to implement.

Accordingly, as one feature of the present invention, there is provided an electromagnetic and radiation shielding system, the system comprising (a) a single enclosure shaped to define a room interior, the room interior being externally accessible through a single passageway, and (b) a door assembly for selectively enclosing the single passageway, (c) wherein the door assembly cooperates with the single enclosure to form an electromagnetic barrier around the room interior in all directions, (d) wherein the door assembly cooperates with the single enclosure to form a radiation barrier around the room interior in all directions.

As another feature of the present invention, there is provided a door assembly for an electromagnetic and radiation shielded enclosure, the enclosure being shaped to define a room interior which is accessible through a single passageway, the enclosure comprising an electromagnetic shield and a radiation shield, door assembly comprising (a) a frame mounted onto the enclosure within the single passageway, the frame being in conductive contact with the electromagnetic shield in the enclosure, (b) a door adapted to be displaced between an open position and a closed position, the door comprising a layer of radiation shielding material, the door having a rear face which includes a conductive portion, and (c) a seal for selectively establishing continuous, peripheral, conductive contact between the frame and the conductive portion of the door when the door is disposed in its closed position.

Various other features and advantages will appear from the description to follow. In the description, reference is made to the accompanying drawings which form a part thereof, and in which is shown by way of illustration, an embodiment for practicing the invention. The embodiment will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings, wherein like reference numerals represent like parts.

DETAILED DESCRIPTION OF THE INVENTION

Electromagnetic and Radiation Shielding System 11

Figure 1:
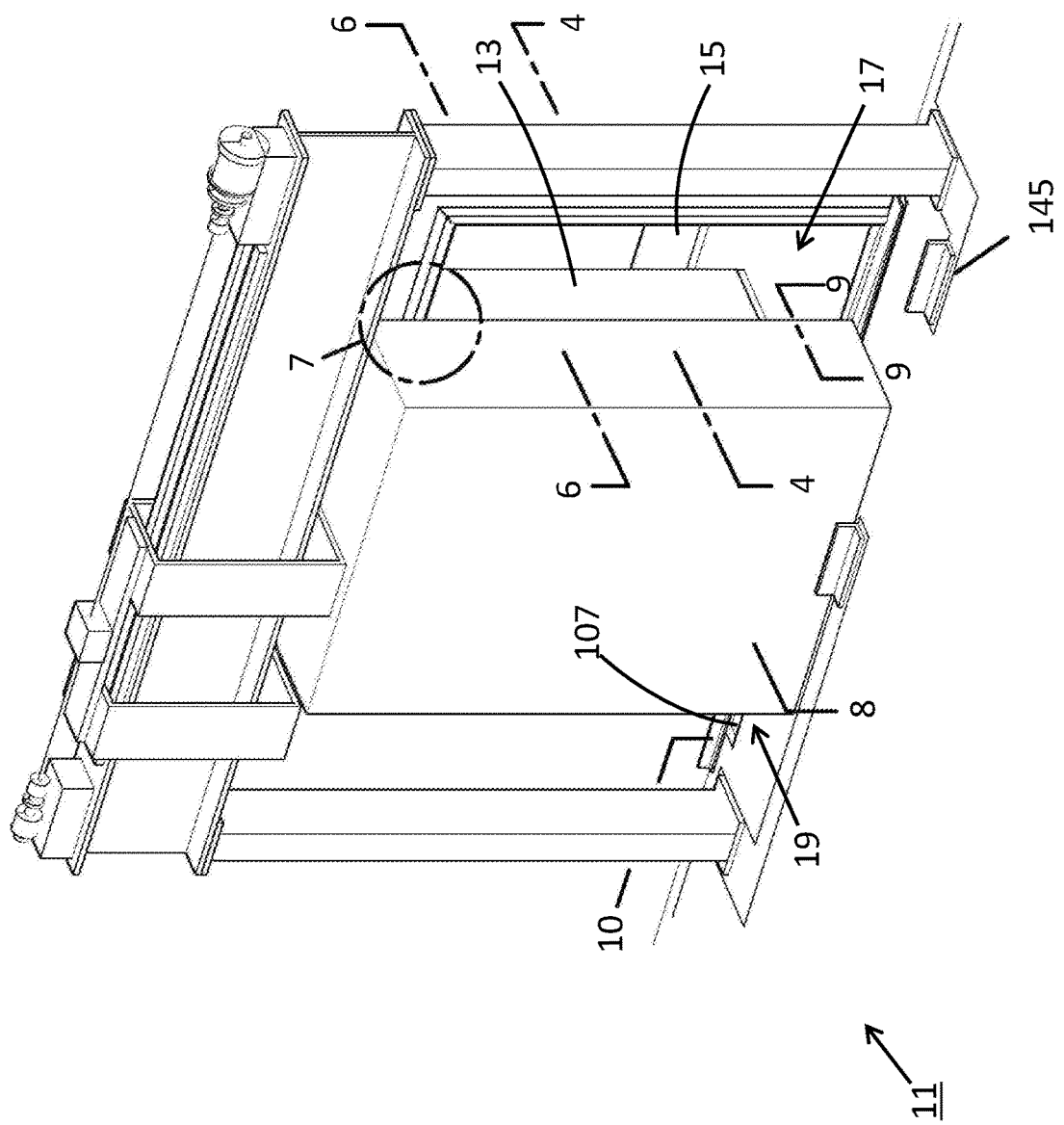
FIG. 1 is a fragmentary, front perspective view of an electromagnetic and radiation shielding system constructed according to the teachings of the present invention, the system being shown with its door disposed in a partially open position.
Figure 2:
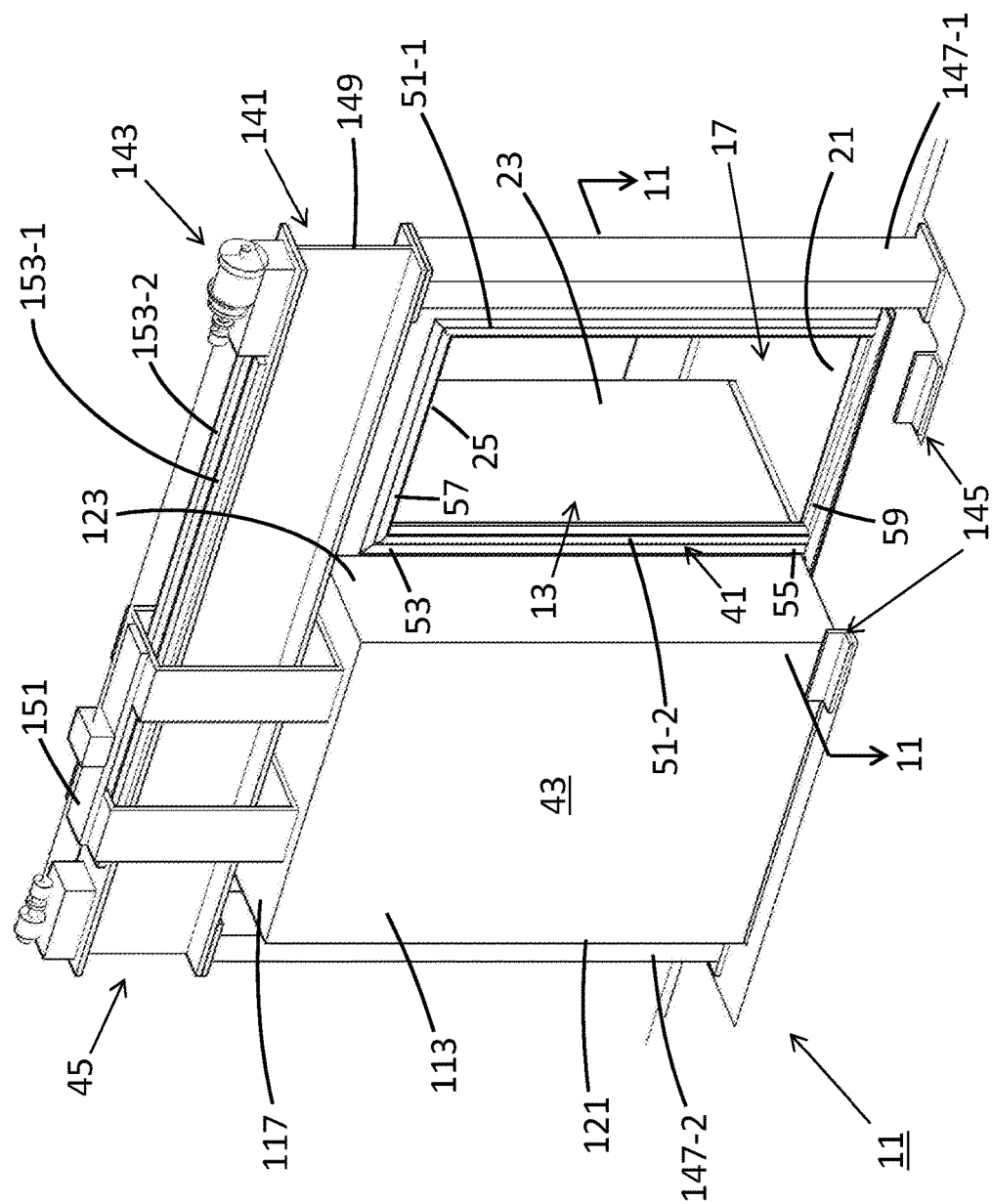
FIG. 2 is a fragmentary, front perspective view of the electromagnetic and radiation shielding system shown in FIG. 1, the door being shown in its fully open position.

Referring now to FIGS. 1 and 2, there is shown an electromagnetic and radiation shielding system, the system being constructed according to the teachings of the present invention and identified generally by reference numeral 11. As will be explained in detail below, system 11 is uniquely designed to provide a single-door solution for a combined electromagnetic and radiation shielded enclosure. In this capacity, system 11 is particularly well-suited for integration in a hybrid detection and treatment room within a medical facility.

In the description that follows, system 11 is described primarily in connection with the shielding of electromagnetic energy which falls within the radio frequency (RF) spectrum. However, it is to be understood that the electromagnetic shielding capabilities of system 11 are not limited to RF energy, but rather could be similarly applied to block other forms of potentially-interfering electromagnetic energy (e.g. microwaves) without departing from the spirit of the present invention.

As can be seen, system 11 comprises (i) an enclosed room, or enclosure, 13 shaped to define a room interior 15, room interior 15 being externally accessible through a single passageway 17, and (ii) a door assembly 19 for selectively enclosing passageway 17. As will be explained in detail below, system 11 is uniquely designed to provide both electromagnetic and radiation shielding capabilities to a common room which is adapted to be selectively enclosed by a single door.

The previously unforeseen ability to provide a single-door solution for a combined electromagnetic and radiation shielded enclosure is highly desirable for a multitude of factors including, but not limited to, the creation of a simpler means of room entrance and egress (i.e. in comparison to multi-door designs). As a result of its simplified means of access, system 11 provides an increase in the amount of room operability and higher patient turnover.

Enclosure 13

As seen most clearly in FIG. 2, enclosed room, or enclosure, 13 is constructed with a foundation, or flooring, 21, a plurality of walls 23 and a ceiling 25 which together define room interior 15. As noted above, room interior 15 is accessible via a single passageway 17, thereby creating a quicker means of entrance and egress, which is highly desirable.

Figure 3:
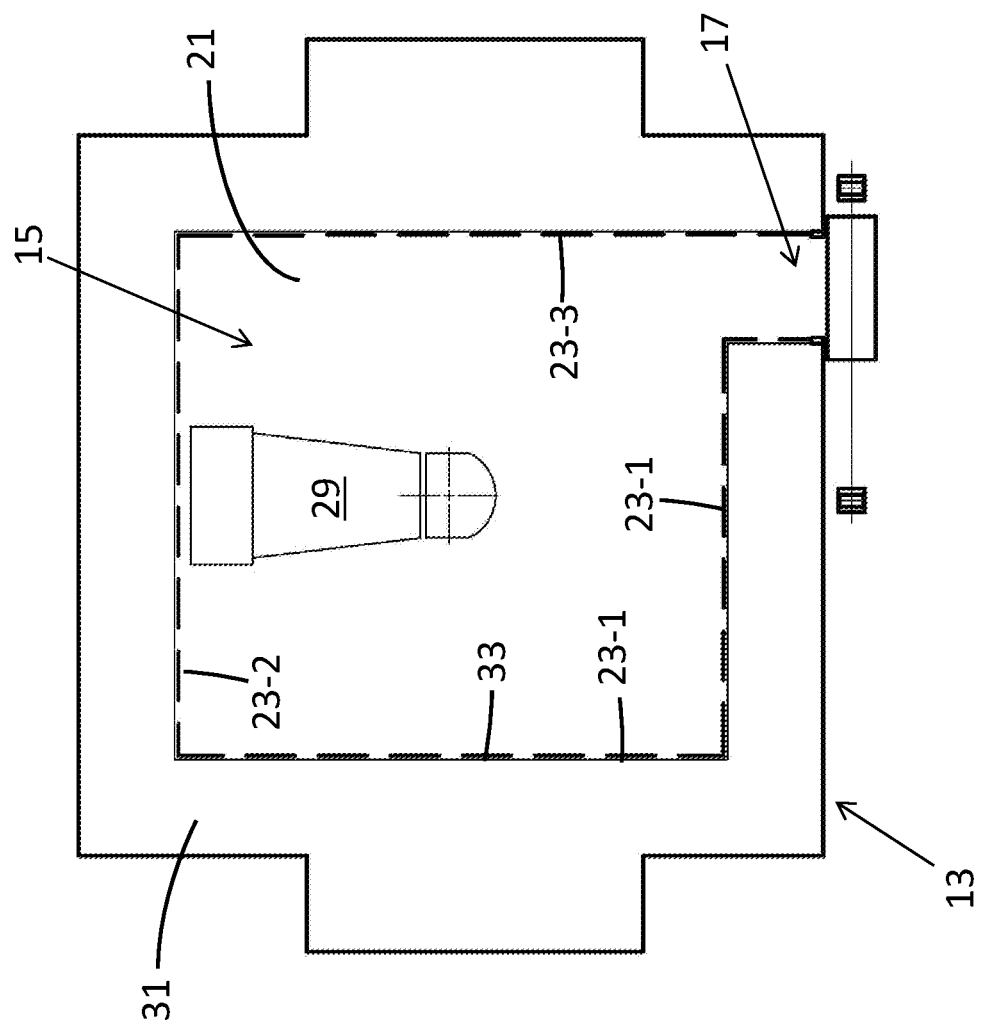
FIG. 3 is a simplified plan view of the electromagnetic and radiation shielding system shown in FIG. 1, the plan view being useful in illustrating a layout for the enclosure.

It should be noted that the size and configuration of flooring 21, walls 23 and ceiling 25 could be in any form. For example, in FIG. 3, there is shown a sample layout for enclosure 13 in which room interior 15 is defined by flooring 21, four walls 23-1 thru 23-4, and a ceiling (not shown). However, it is to be understood that the dimensional requirements of enclosure 13 could be varied, as needed, to suit the needs of the particular application (e.g., based on the size of equipment housed therein and/or footprint restrictions within the medical facility). For instance, in FIG. 3, enclosure 13 is dimensioned to house a piece of medical equipment 29.

As a feature of the present invention, enclosure 13 is constructed with both a radiation shield 31 and an electromagnetic shield 33. In this manner, enclosure 13 is particularly well-suited for use as a hybrid diagnostic and treatment room, such as of the type equipped with machines designed to perform both diagnostic and treatment operations (e.g., MR-Linac devices).

As will be explained further in detail below, radiation shield 31 is created by constructing each of flooring 21, walls 23, and ceiling 25 with a layer of radiation-shielding material, such as concrete or lead, that fully surrounds, or encloses, room interior 15 in all directions with the exception of open passageway 17. In this manner, enclosure 13 forms a barrier that prevents the escape of radiation into the surrounding environment.

Additionally, electromagnetic shield 33 is created by incorporating a conductive skin (e.g., a metal sheet, meshing, or screen) into each of flooring 21, walls 23, and ceiling 25. The conductive skin is dimensioned and configured in each of flooring 21, walls 23, and ceiling 25 so as to form a continuous peripheral barrier around the entirety of room interior 15 in all directions with the exception of open passageway 17.

Figure 4:
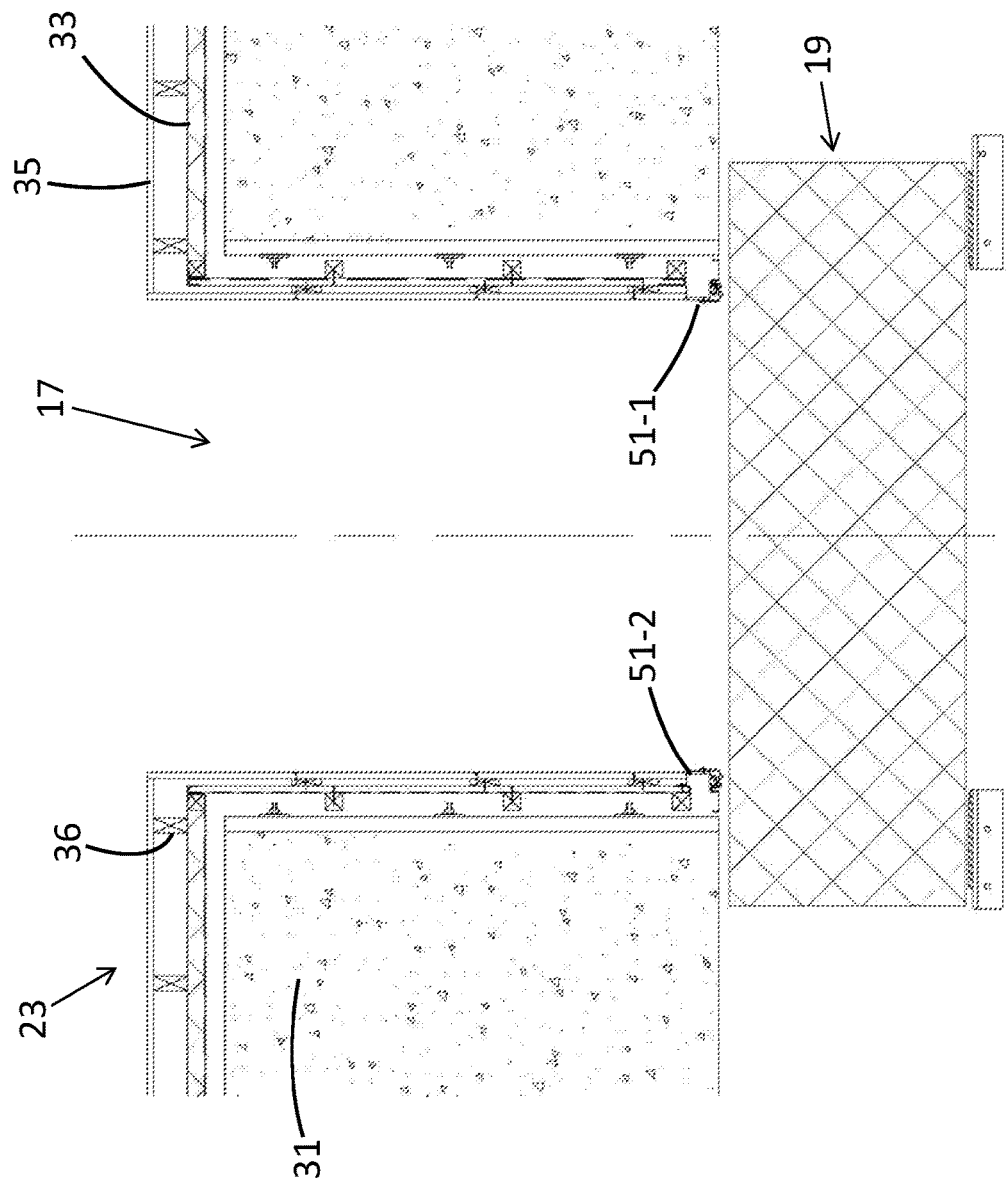
FIG. 4 is a section view of the electromagnetic and radiation shielding system shown in FIG. 1, taken along lines 4-4.

Referring now to FIG. 4, a portion of a wall 23 is shown which is useful in understanding how enclosure 13 could be constructed to include both radiation shield 31 and electromagnetic shield 33. Specifically, in wall 23, radiation shield 31 is formed as an enlarged structure of radiation-shielding material, such as pour-in-place concrete, of a sufficient depth so as to prevent the emission of radiation therethrough.

Furthermore, in wall 23, electromagnetic, or radio frequency (RF), shield 33 is formed as an enlarged plate of conductive material, such as cooper or galvanized steel, which is fixedly secured to the interior of radiation shield 31 in a spaced apart relationship relative thereto (e.g. via non-ferrous plywood battens). A finished interior panel 35, constructed of drywall or other suitable material, is then fixedly secured to the interior of electromagnetic shield 33 in a spaced apart relationship relative thereto (e.g. via non-ferrous plywood battens 36). In this manner, the interior of enclosure 13 has an aesthetically pleasing appearance.

For simplification purposes only, the particular means for integrating radiation shield 31 and electromagnetic shield 33 is described above in connection with only a single wall 23. However, it is to be understood that similar means for incorporating radiation shield 31 and electromagnetic shield 33 could be applied to flooring 21, remaining walls 23, and ceiling 25 as part of the present invention.

As referenced briefly above, room interior 15 is accessible through a single passageway 17. Accordingly, in view of the construction of enclosure 13, as set forth in detail above, passageway 17 serves as the only means for electromagnetic energy and/or radiation to traverse enclosure 13. Therefore, door assembly 19 serves two primary functions within electromagnetic and radiation shielding system 11. First, door assembly 19 serves as structural barrier for selectively enclosing passageway 17 and thereby prevent entrance into and egress from room interior 15 by an individual. Second, door assembly 19 is uniquely designed to both (i) establish peripheral conductive contact with electromagnetic shield 33 in enclosure 13 and thereby complete an electromagnetic barrier around room interior 15, and (ii) physically overlap the remainder of radiation shield 31 in enclosure 13 and thereby complete a radiation barrier around room interior 15. In this capacity, door assembly 19 provides enclosure 13 with full electromagnetic and radiation shielding capabilities, which is a principal feature of the present invention. The particular means by which door assembly 19 interfaces with enclosure 13 so as to provide full, continuous electromagnetic and radiation shielding capabilities surrounding room interior 15 is set forth in detail below.

Door Assembly 19

As seen most clearly in FIG. 2, door assembly 19 comprises (i) a four-sided, continuous metal frame 41 secured within the opening in passageway 17 in conductive contact with electromagnetic shield 33, (ii) a single door 43 adapted to slide between an open position, in which passageway 17 remains open for entrance and/or egress therethrough, and a closed position, in which door 43 not only physically encloses passageway 17 but also establishes complete peripheral conductive contact with frame 41, and (iii) a support structure assembly 45 for holding and driving door 43 along a fixed travel path between its open and closed positions.

As can be seen, frame 41 is secured within the opening of passageway 17 and comprises (i) a pair of upright, opposing jambs, or side posts, 51-1 and 51-2, each jamb 51 having a top end 53 and a bottom end 55, (ii) a horizontal header, or head, 57 extending horizontally across the top of passageway 17 in contact with the top ends 53 of jambs 51, and (iii) a sill, or threshold, 59 mounted in flooring 21 within the opening of passageway 17 in contact with bottom ends 55 of jambs 51. As will be explained further below, because frame 41 forms a continuous, four-sided, metal structure within the opening of passageway 17 which is maintained in conductive contact with electromagnetic shield 33, disposing door 43 in peripheral conductive contact with frame 41 can be used to create an electromagnetic shield around the entirety of room interior 15.

Figure 5:
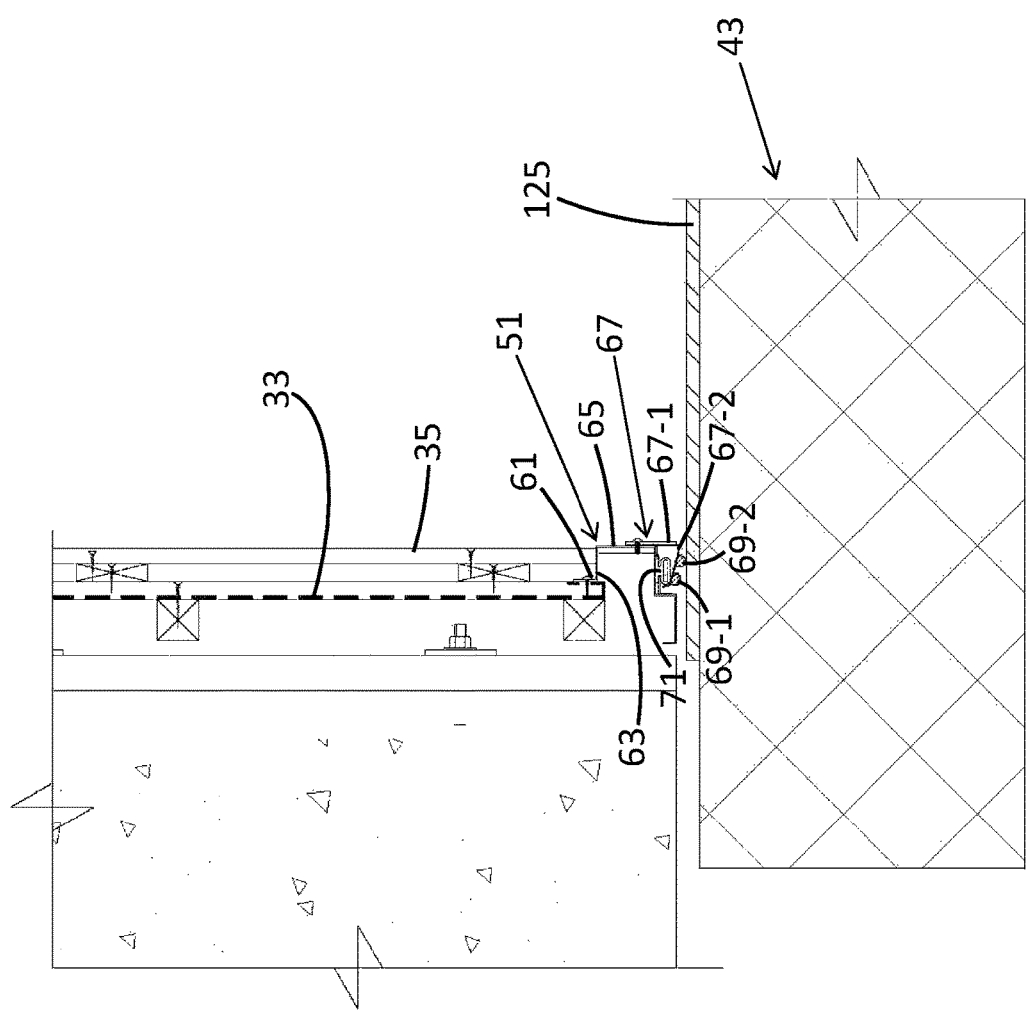
FIG. 5 is an enlarged, fragmentary section view of the electromagnetic and radiation shielding system shown in FIG. 4, the section view being useful in illustrating the articulating conductive seal established between each jamb and the door.

Referring now to FIGS. 2, 4 and 5, each jamb 51 is constructed as an elongated, multi-faced strip of conductive material, such as stainless steel, that is fixedly secured to the interior surface of electromagnetic shield 33 along a corresponding side of passageway 17. More specifically, as shown in FIG. 5, jamb 51 is shaped to define a rearward flange 61 which is disposed flush against the front edge of RF shielding 33 and is fixedly secured thereto by a fastening element, such as a screw. In this capacity, one jamb 51 is conductively coupled to electromagnetic shield 33 along the entire length of each side of open passageway 17. As can be seen, flange 61 is inwardly offset by a spacer segment 63 such that its interior planar surface 65 lies flush with finished interior panel 35.

As a feature of the present invention, each jamb 51 is equipped with means for establishing articulating conductive contact with the interior face of door 43. Specifically, an L-shaped articulating member, or spring, 67 is connected to jamb 51 and extends the entirety of its length. As can be seen, spring 67 includes a fixed portion 67-1, which is fixedly secured to interior planar surface 65 by one or more fastening elements (e.g., a screw), and an articulating portion 67-2, which is adapted to pivot relative to fixed portion 67-1.

A pair of elongated conductive gaskets, or seals, 69-1 and 69-2, each generally circular in lateral cross-section, is secured onto the exposed front surface of articulating portion 67-2 and extends the entirety of its length. Each gasket 69 is preferably constructed with a compressible foam core which is encased within an outer shell of a metallized fabric material.

A pneumatic actuator, or bladder, 71 projects out from the front of jamb 51 and into contact against the rear surface of articulating portion 67-2. Pneumatic actuator 71 is, in turn, is connected by one or more airline hoses to a common pneumatic supply source (e.g., an air compressor) for system 11. As will be explained in detail below, the delivery of air into pneumatic actuator 71 pivots articulating portion 67-2 of spring 67 forward such that gaskets 69 establish continuous, linear contact against the interior face of door 43 along the entire side of passageway 17.

Figure 6:
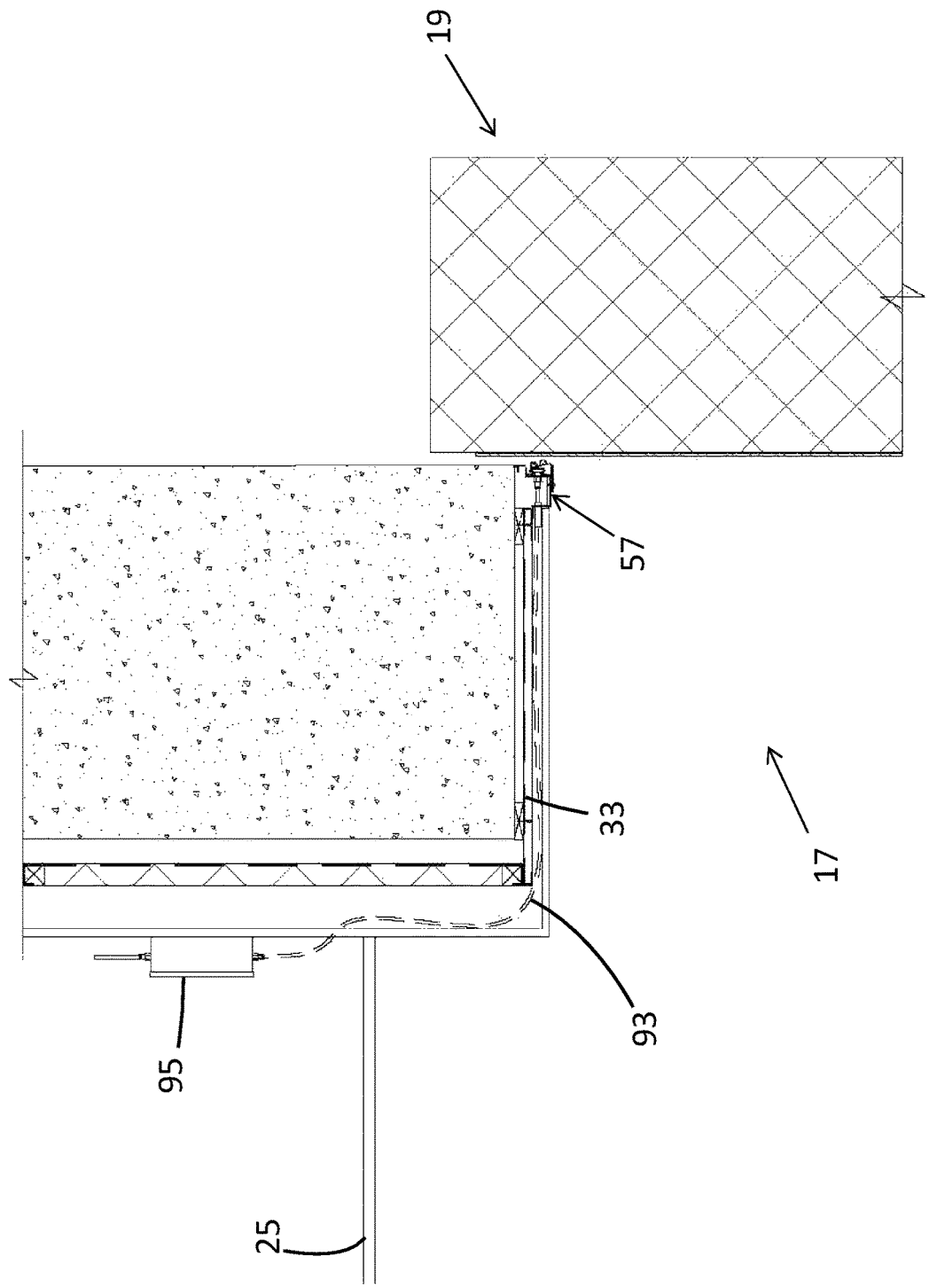
FIG. 6 is a section view of the electromagnetic and radiation shielding system shown in FIG. 1, taken along lines 6-6.
Figure 7:
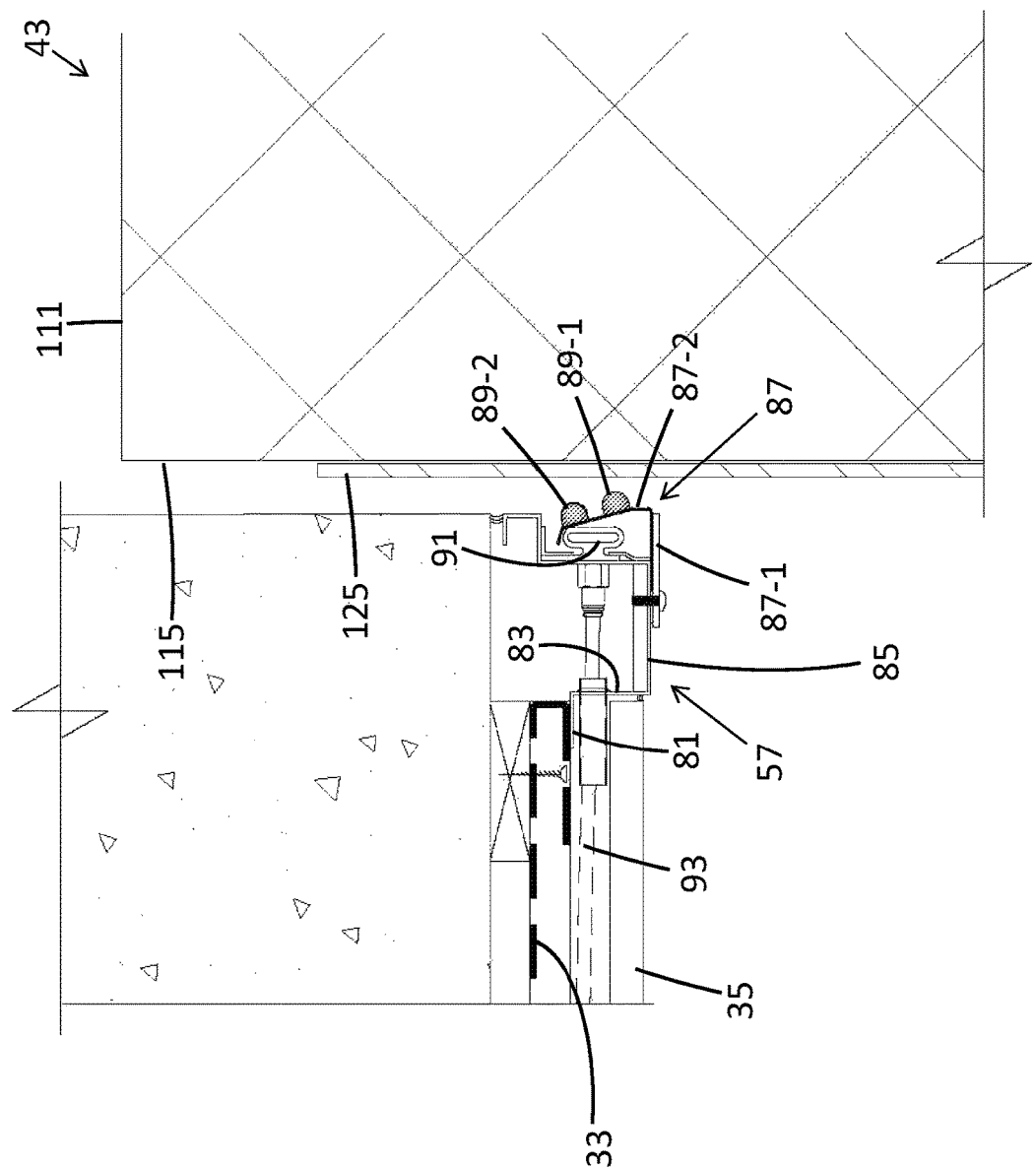
FIG. 7 is an enlarged, fragmentary section view of the electromagnetic and radiation shielding system shown in FIG. 6, the section view being useful in illustrating the articulating conductive seal established between the header and the door.

As referenced previously, header 57 extends horizontally across the top of passageway 17 in conductive contact with the top ends 53 of jambs 51. Referring now to FIGS. 2, 6, and 7, header 57 is constructed as an elongated, multi-faced strip of conductive material, such as stainless steel, that is fixedly secured to the interior surface of electromagnetic shield 33 along the top of passageway 17. As shown in FIG. 7, header 57 is shaped to define a rearward flange 81 which is disposed flush against the underside of RF shielding 33 along its front edge and is fixedly secured thereto by one or more fastening elements, such as a screw. In this capacity, header 57 is conductively coupled to electromagnetic shield 33 along the entire top edge of open passageway 17. As can be seen, flange 81 is inwardly offset by a spacer segment 83 such that its interior planar surface 85 lies flush with finished interior panel 35.

Similar to each of jambs 51, header 57 is also equipped with means for establishing articulating conductive contact with the interior face of door 43. Specifically, an L-shaped articulating member, or spring, 87 is connected to header 57 and extends the entirety of its length. As can be seen, spring 87 includes a fixed portion 87-1, which is fixedly secured to interior planar surface 85 by one or more fastening elements (e.g., a screw), and an articulating portion 87-2, which is adapted to pivot relative to fixed portion 87-1.

A pair of elongated conductive gaskets, or seals, 89-1 and 89-2, each generally circular in lateral cross-section, is secured onto the exposed front surface of articulating portion 87-2 and extends the entirety of its length. Similar to gaskets 69, each gasket 89 is preferably constructed with a compressible foam core which is encased within an outer shell of a metallized fabric material.

A pneumatic actuator, or bladder, 91 projects out from the front of header 57 and into contact against the rear surface of articulating portion 87-2. Pneumatic actuator 91 is, in turn, is connected by an airline hose 93 to a common pneumatic supply source (e.g., an air compressor) for system 11. As shown in FIG. 6, airline hose 93 may be connected to a quick-release valve box 95 which, in turn, is connected to a control box in fluid communication with the air supply source. In this manner, air delivery can be regulated by the operator. As will be explained in detail below, the delivery of air into pneumatic actuator 91 pivots articulating portion 87-2 of spring 87 forward such that gaskets 89 establish continuous, linear contact against the interior face of door 43 along the top of passageway 17.

Figure 8:
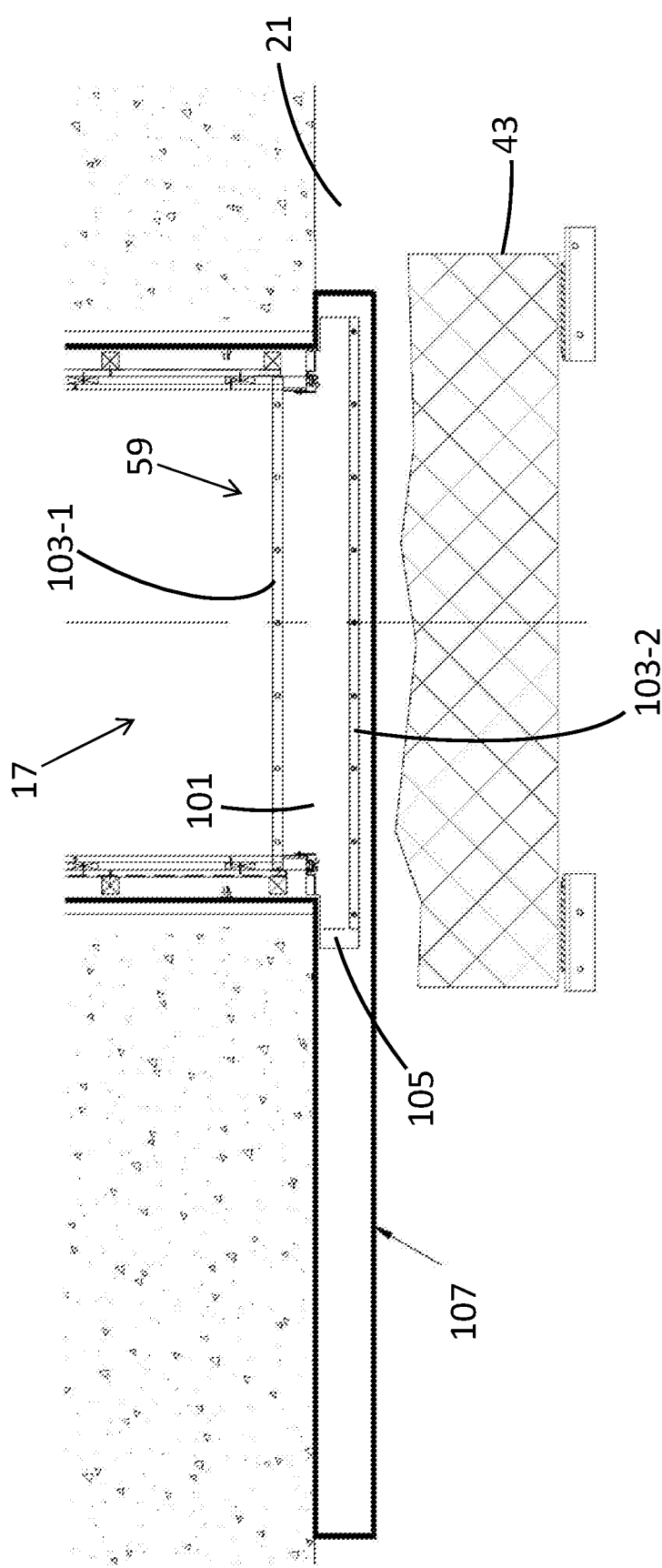
FIG. 8 is a section view of the electromagnetic and radiation shielding system shown in FIG. 1, taken along lines 8-8.
Figure 9:
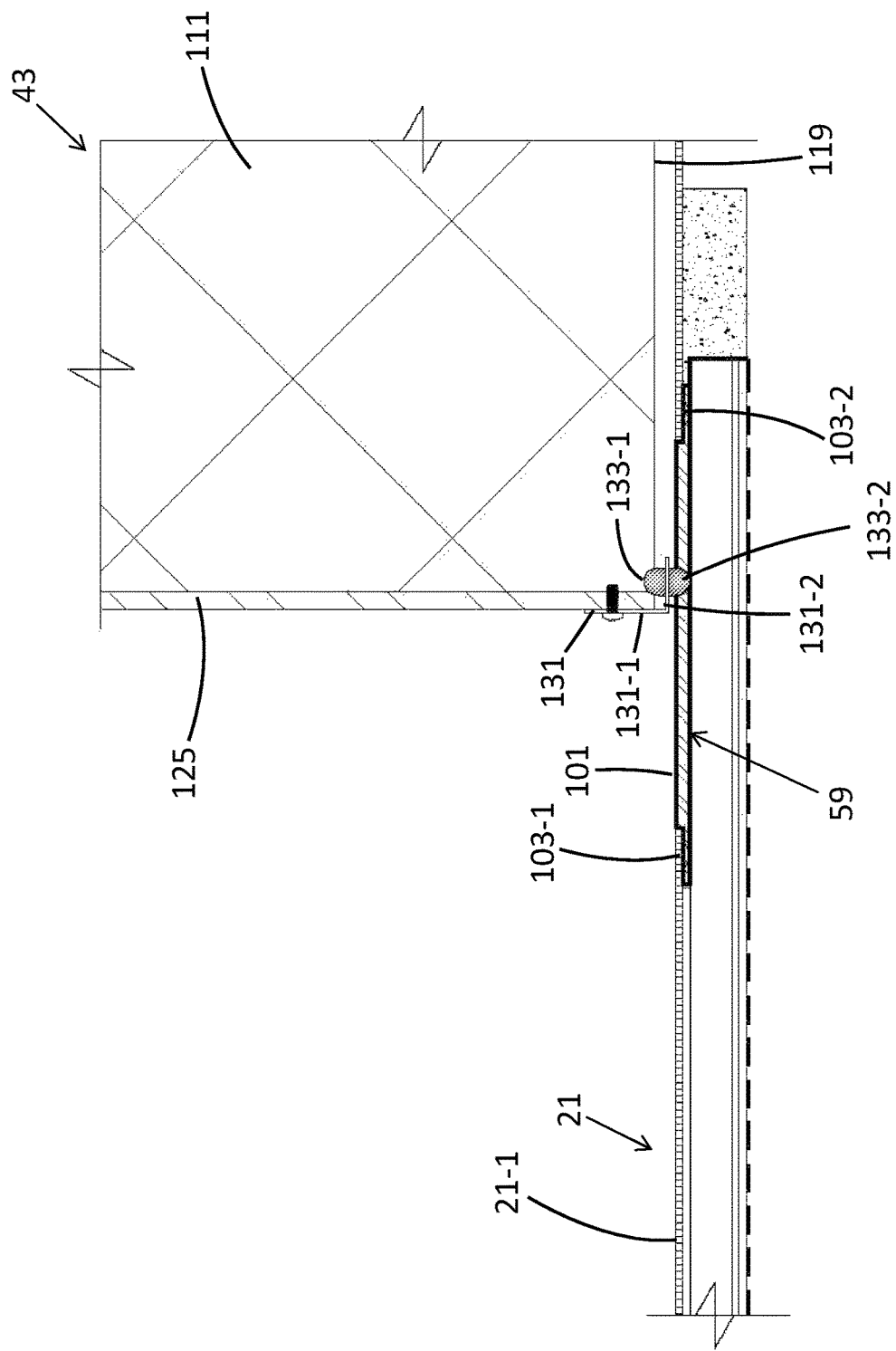
FIG. 9 is a section view of the electromagnetic and radiation shielding system shown in FIG. 1, taken along lines 9-9.

As noted above, sill 59 is mounted in flooring 21 within the opening of passageway 17 in contact with bottom ends 55 of jambs 51. Referring now to FIGS. 2, 8 and 9, sill 59 is constructed as an elongated, unitary, generally rectangular plate of conductive material, such as stainless steel, that is installed in flooring 21 so as to extend across the threshold of passageway 17.

As shown in FIGS. 8 and 9, sill 59 includes a widened central section 101, a chamfered inner edge 103-1 and a chamfered outer edge 103-2. As seen most clearly in FIG. 9, chamfered edges 103 enable finished surface 21-1 of flooring 21 to lie in a coplanar relationship with central section 101 of sill 59 (i.e. for safety and aesthetic purposes).

Figure 10:
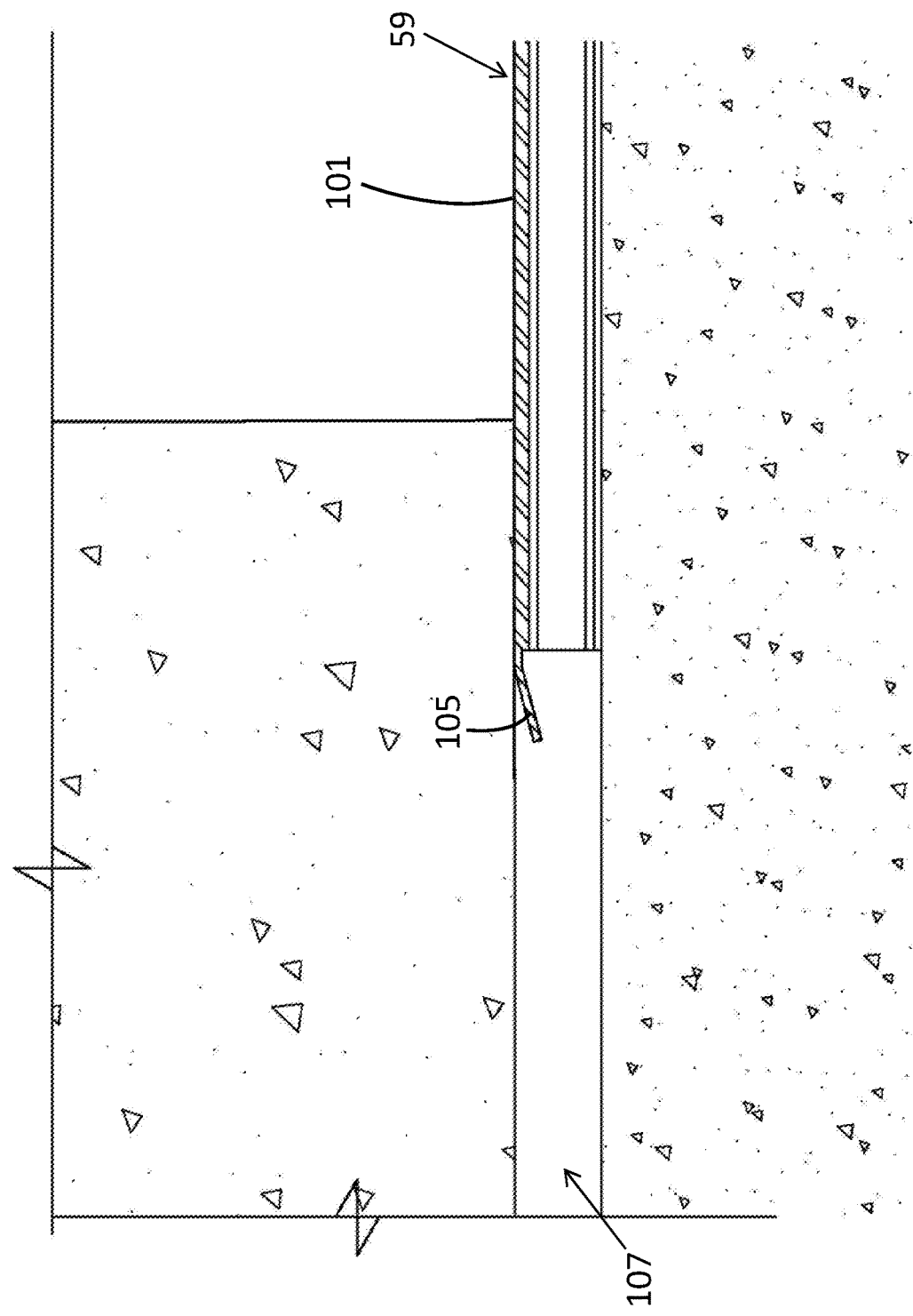
FIG. 10 is a section view of the electromagnetic and radiation shielding system shown in FIG. 1, taken along lines 10-10.

As shown in FIGS. 8 and 10, sill 59 additionally includes a taper, or wing, 105 which is formed onto the left end of central section 101 and extends downwardly therefrom at an acute angle. Sill taper 105 projects into a six-inch wide, rectangular recess 107 which is formed into flooring 21 immediately outside of enclosure 13 in alignment with sill 59. As will be explained in detail below, recess 107 and sill taper 105 assist in the process of establishing selective conductive contact between sill 59 and door 43.

As referenced above, door 43 is designed to serve as both a physical barrier for limiting entrance into and egress from room interior 15 as well as means for establishing an electromagnetic and radiation shield across passageway 17, thereby completing the electromagnetic and radiation barrier around the entirety of room interior 15. Due to the significant weight of door, as a result of its radiation shielding properties, unique design features have been incorporated into system 11 to create an RF shield across passageway 17, particularly along its threshold, as will be explained further below.

As seen in FIGS. 2, 7, and 9, door 43 is constructed as an enlarged, unitary structure which is of a height and width (e.g., 72 inches) so as to overlap and thereby enclose open passageway 17 when door is disposed in its closed position. As represented herein, door 43 comprises an enlarged slab 111 of a suitable radiation shielding material, such as concrete.

However, it should be noted that, in lieu of a single slab of radiation shielding material, door 43 could be constructed using alternative techniques to derive its radiation shielding properties. For instance, door 43 could be alternatively constructed by disposing a plurality of parallel lead plates within a hollow, slab-like enclosure. It is to be understood that these alternative constructions for door 43 fall within the scope of the present invention.

Slab 111 is represented herein as comprising a front face, 113, a rear face 115, a top face 117, a bottom face 119, a left-side face 121 and a right-side face 123. As a feature of the present invention, a conductive plate 125 is mounted on rear face 115. As will be explained further below, plate 125 provides door 43 with its RF shielding capabilities.

Plate 125 is constructed of any suitable conductive material, such as stainless steel. Plate 125 is dimensioned so as to extend just beyond frame 41 when door 43 is disposed in its closed position. In this manner, plate 125 forms a continuous RF shield across open passageway 17 when door 43 is disposed in its closed position.

As a feature of the present invention, door 43 is equipped with means for establishing conductive contact between plate 125 and sill 59. Specifically, as seen most clearly in FIG. 9, an L-shaped bracket 131 is connected to plate 125 along the entirety of its bottom edge. Bracket 131 is constructed of a suitable conductive material, such as stainless steel, and includes a vertical portion 131-1, which is fixedly secured to plate 125 along its bottom edge by at least one fastening element, and a horizontal portion 131-2 which extends beneath bottom face 119 of slab 111 in a spaced apart relationship relative thereto.

A pair of elongated conductive gaskets, or seals, 133-1 and 133-2, each generally circular in lateral cross-section, is secured onto opposing surfaces of horizontal portion 131-2 along the entirety of its length. Each gasket 133 is preferably constructed with a compressible foam core which is encased within an outer shell of a metallized fabric material. Therefore, as can be seen, upper gasket 133-1 serves to maintain continuous conductive contact with metal plate 125 on door 43 and lower gasket 133-2 is designed to selectively establish conductive contact with sill 59.

Although bracket 131 is shown herein as maintaining gaskets 133 fixed in position relative to door 43, it is to be understood that non-static means for establishing a releasable seal between plate 125 and sill 59 could be implemented without departing from the spirit of the present invention. For instance, it is envisioned that bracket 131 could be modified in its design to allow for articulation. In turn, a pneumatic actuator could be integrated into door assembly 19 in order to selectively displace the articulating bracket such that gaskets 133 are drawn into contact with sill 59.

As noted above and as shown in FIG. 10, sill 59 is provided with a taper 105 along its left end which protrudes into a recess 107 formed in flooring 21. Accordingly, as door 43 transitions from its closed position to its open position, lower gasket 133-2 travels along taper 105 and ultimately projects into recess 107. By minimizing the frictional forces applied onto lower gasket 133-2, which are directly attributable to the significant weight of radiation-shielding slab 111 (in the order of several to tens of thousands of pounds), the effective lifespan system 11 can be extended, which is highly desirable.

Referring back to FIG. 2, system 11 includes a support structure assembly 45 for holding and driving door 43 along a fixed travel path between its open and closed positions. More specifically, support structure assembly 45 comprises (i) a support structure 141, disposed immediately outside of enclosure 13, for retaining door 43, (ii) a drive mechanism 143, coupled to support structure 141, for displacing door 43 between its open and closed positions, and (iii) a plurality of door guides 145, installed on flooring 21 just outside of enclosure 13, for restricting displacement of door 43 along a linear travel path.

In the present embodiment, support structure 141 is represented as comprising (i) a pair of vertically-configured steel members, or columns, 147-1 and 147-2 which are installed on flooring 21 just outside of enclosure 13 on opposite sides of passageway 17, and (ii) a horizontally-configured steel member, or beam, 149 mounted onto and secured to the distal ends of columns 147 directly above passageway 17. Preferably, the construction columns 147 and beam 149, as well as their means of interconnection, are designed to support the considerable weight of door 43.

Support structure 141 additionally includes a beam trolley 151 which is permanently secured (e.g., welded) onto top face 117 of door 43. Trolley 151 is additionally adapted to travel within a pair of spaced apart, longitudinal tracks 153-1 and 153-2 formed in beam 149 (e.g., using one or more rollers).

Drive mechanism 143 is mounted onto opposing ends of beam 149 and is connected to trolley 151. As can be appreciated, activation of drive mechanism 143 serves to displace door 43 between its open and closed positions.

Figure 11:
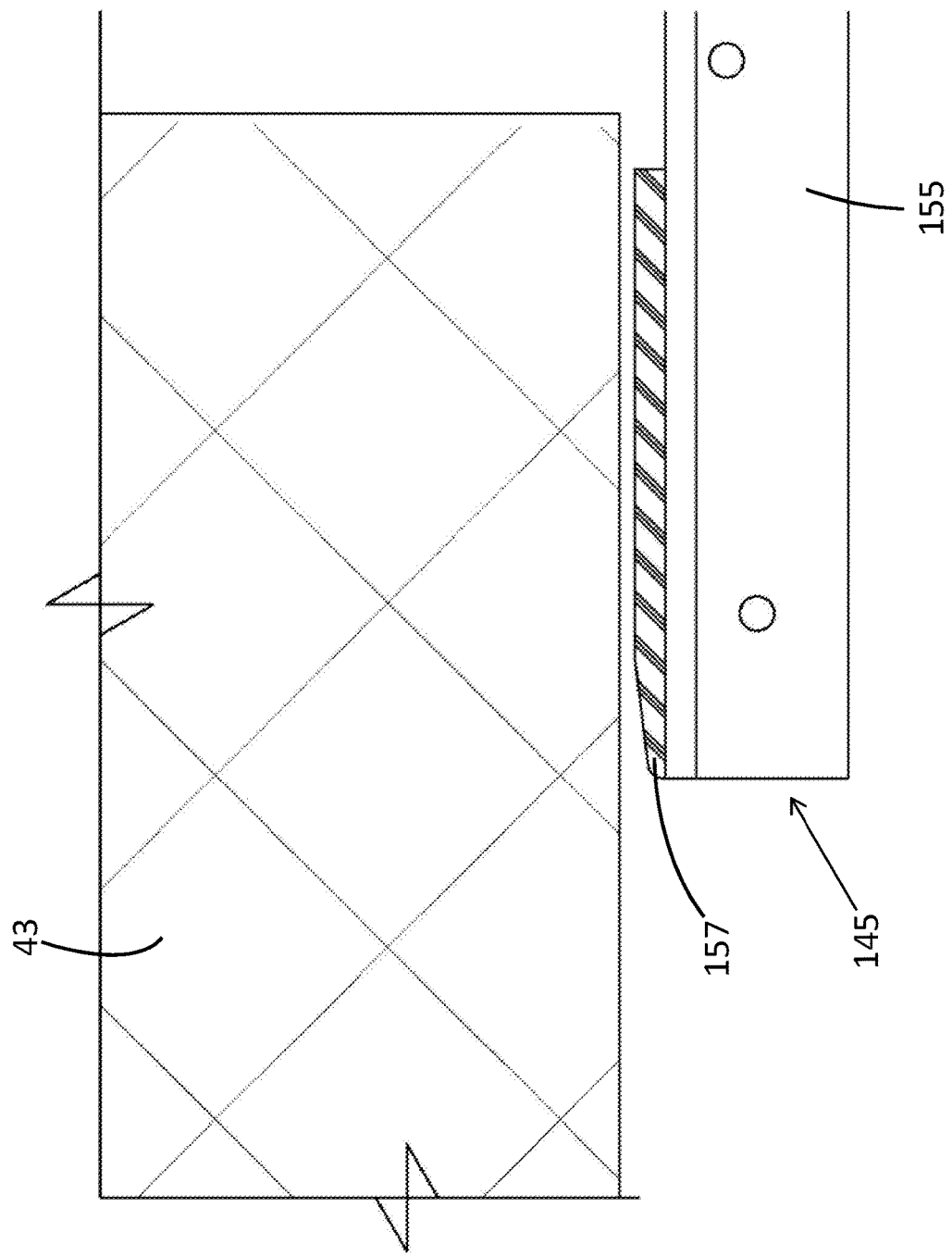
FIG. 11 is a fragmentary, section view of the electromagnetic and radiation shielding system shown in FIG. 2, taken along lines 11-11.

Door guides 145 are installed onto flooring 21 to restrict travel of door 43 between its open and closed positions along a linear path. As shown in FIG. 11, each door guide 145 is represented as a unitary, L-shaped member that includes a horizontal portion 155 and a vertical portion 157.

Horizontal portion 155 of each door guide 145 lies flat against and is permanently affixed to flooring 21 in its desired location relative to door 43. Vertical portion 157 therefore applies continuous contact against door 43 so as to restrict its travel along a linear path. Preferably, vertical portion 157 is constructed, or is applied with a coating, of a suitable material (e.g., plastic) that ensures its durability as well as minimizes frictional forces imparted onto door 43.

Operation of System 11

In use, system 11 is designed to operate in the following manner. With door 43 disposed in its open position, individuals (e.g. patients, healthcare personnel, etc.) are able to quickly and easily enter into and/or exit from room interior 15 though single passageway 17. It is also important to note that, with door 43 disposed in its open position, lower gasket 133-2 on door 43 aligns within recess 107 in flooring 21, thereby minimizing the degree of wear and tear imparted thereon.

Thereafter, in order to engage in any diagnostic and/or treatment activities, it is required that door 43 be disposed in its closed position. Accordingly, an operator initiates closing of door 43 via an externally-mounted control panel (not shown). In response thereto, the control panel activates drive mechanism 143 which, in turn, displaces door 43 laterally into its closed position along the generally linear path defined by guides 145. It should be noted that as door 43 is displaced laterally into its closed position, lower gasket 133-2 eventually abuts against the top surface of taper 105 and ultimately slides on top of central section 101 of sill 59.

Once door 43 aligns directly in front of passageway 17, sensors (not shown) in electrical communication with the control panel deactivate drive mechanism 143, thereby precluding any further displacement of door 43. With door 43 disposed in its closed position, it is to be understood that the dimensions of door 43 are such that door 43 completely encloses passageway 17. Furthermore, because door 43 overlaps radiation shield 31 in enclosure 13, a fully encompassing radiation shield is effectively formed around the entirety of room interior 15. As a result, any radiation produced by equipment located within room interior 15 is prevented from escaping into the ambient environment.

Thereafter, the control panel activates the common pneumatic supply source and delivers a supply of air to each of pneumatic actuators 71 and 91. As referenced previously, the inflation of pneumatic actuators 71 urges conductive gaskets 69 into linear contact against plate 125 along the entire side of passageway 17. Additionally, the inflation of pneumatic actuator 91 urges conductive gaskets 89 into linear contact against plate 125 along the entire top edge, or head, of passageway 17. Lastly, as noted above, lower gasket 133-2 on door 43 is disposed in linear contact against central section 101 of sill 59 along the entirety of its length.

As a result, a continuous region of conductive contact (i.e. a conductive seal) is thereby established between frame 41 and plate 125 on door 43. Because frame 41 is, in turn, conductively coupled to RF shield 33, a fully encompassing electromagnetic shield is effectively formed around the entirety of room interior 15. As a result, electromagnetic energy, which may otherwise create RF interference, is incapable of transmission into or from room interior 15.

Upon completion of diagnostic and/or treatment activities within room interior 15, door 43 is returned to its open position by the operator using the control panel. In response, the control panel causes quick-release valve box 95 to release air supplied to pneumatic actuators 71 and 91. Due to the resilient nature of springs 67 and 87, gaskets 69 and 89 are thereby drawn out of contact from plate 125 on door 43 which, in turn, disrupts (i.e. opens) the electromagnetic shield.

With gaskets 69 and 89 disengaged from plate 125, the control panel causes drive mechanism 143 to initiate displacement of door 43 into its open position along the generally linear path defined by guides 145 which, in turn, disrupts (i.e. opens) the radiation shield. As referenced previously, as door 43 is displaced open, lower gasket 133-2 eventually abuts against the top surface of taper 105 and ultimately projects into recess 107 in flooring 21 to minimize wear and tear. Once door 43 is detected by sensors as reaching its fully open position, the control panel deactivates the drive mechanism 143 which, in turn, terminates displacement of door 43. Thereafter, free access to room interior 15 is permitted.

The invention described in detail above is intended to be merely exemplary and those skilled in the art shall be able to make numerous variations and modifications to it without departing from the spirit of the present invention. All such variations and modifications are intended to be within the scope of the present invention as defined in the appended claims.

For instance, in the present embodiment, means for establishing articulating conductive contact along the sides and head of passageway 17 is integrated into each of jambs 51 and header 57 of frame 41. However, it is to be understood that means for establishing articulating conductive contact could be similarly integrated into door assembly 19, instead of frame 41, without departing from the spirit of the present invention.

Additionally, in the present embodiment, door assembly 19 is shown as comprising a single slidable door 43 for enclosing passageway 17. However, it is to be understood that door assembly 19 could utilize alternative types of door constructions (e.g., bi-parting sliding doors, unitary swing doors, and the like) without departing from the spirit of the present invention.

Furthermore, in the present embodiment, pneumatic actuators 71 and 91 are represented as inflatable bladders. However, it should be noted that actuators 71 and 91 need not be limited to the use of inflatable bladders to help create a releasable seal between door 43 and frame 41. Rather, it is to be understood that alternative types of pneumatic actuators (e.g., air cylinders) could be used in place thereof without departing from the spirit of the present invention.

What is claimed is:

1. An electromagnetic and radiation shielding system, the system comprising:
    (a) a single enclosure shaped to define a room interior, the single enclosure including a flooring, a plurality of walls, and a ceiling which together define the room interior, each of the flooring, the plurality of walls and the ceiling including a radiation shield and an electromagnetic shield, the room interior being externally accessible through a single passageway; and
    (b) a single door assembly for selectively enclosing the single passageway, the single door assembly comprising;
        (i) a frame mounted onto the single enclosure within the single passageway, the frame being in conductive contact with the electromagnetic shield, and
        (ii) a door adapted to be displaced between an open position and a closed position, the door comprising a slab with high-energy radiation shielding properties, the slab having a front face, a rear face, a top face, a bottom face, a left-side face, and a right-side face, the entirety of the rear face being conductive,
        (iii) wherein, in its closed position, the door encloses the single passageway and is adapted to selectively establish continuous, peripheral, conductive contact with the frame;
    (c) wherein the single door assembly cooperates with the single enclosure to form an electromagnetic barrier around the room interior in all directions;
    (d) wherein the single door assembly cooperates with the single enclosure to form a radiation barrier around the room interior in all directions.

2. The electromagnetic and radiation shielding system as claimed in claim 1 wherein the radiation shield is in the form of a layer of radiation-shielding material.

3. The electromagnetic and radiation shielding system as claimed in claim 2 wherein the electromagnetic shield is in the form of a skin of conductive material.

4. The electromagnetic and radiation shielding system as claimed in claim 3, with the door in its closed position, the conductive portion on the rear face of the door is adapted to selectively contact the frame through a continuous conductive seal.

5. The electromagnetic and radiation shielding system as claimed in claim 4 wherein the slab for the door comprises a layer of high-energy radiation shielding material.

6. The electromagnetic and radiation shielding system as claimed in claim 5 wherein the frame comprises:
    (a) a pair of upright, opposing jambs, each jamb having a top end and a bottom end;
    (b) a horizontal header disposed in contact with the top ends of the pair of upright jambs; and
    (c) a sill adapted to be mounted in a flooring within the passageway, the sill being disposed in contact with the bottom ends of the pair of upright jambs.

7. The electromagnetic and radiation shielding system as claimed in claim 6 further comprising:
   (a) an articulating member conductively coupled to each of the pair of upright jambs and the horizontal header; and
   (b) at least one conductive gasket connected to the articulating member,
   (c) wherein, with the door in its closed position, the articulating member is adapted to be displaced such that the at least one conductive gasket is disposed in contact with the conductive portion on the rear surface of the door.

8. The electromagnetic and radiation shielding system as claimed in claim 7 further comprising a pneumatic actuator which is adapted to selectively displace the articulating member coupled to each of the upright jambs and the horizontal header.

9. The electromagnetic and radiation shielding system as claimed in claim 6 further comprising:
   (a) a bracket connected to the door; and
   (b) at least one conductive gasket conductively coupled to the conductive portion on the rear surface of the door;
   (c) wherein, with the door in its closed position, the at least one conductive gasket contacts the sill.

10. An electromagnetic and radiation shielding system, the system comprising:
    (a) a single enclosure, the single enclosure including a flooring, a plurality of walls and a ceiling which together define a room interior, the room interior being externally accessible through a single passageway, each of the flooring, the plurality of walls and the ceiling including a radiation shield and an electromagnetic shield;
    (b) a door assembly for selectively enclosing the single passageway, the door assembly comprising,
       (i) a frame mounted onto the enclosure within the single passageway, the frame being in conductive contact with the electromagnetic shield in the enclosure, the frame comprising,
          (A) a pair of upright, opposing jambs, each jamb having a top end and a bottom end,
          (B) a horizontal header disposed in contact with the top ends of the pair of upright jambs, and
          (C) a sill adapted to be mounted in the flooring within the passageway, the sill being disposed in contact with the bottom ends of the pair of upright jambs, wherein the sill comprises a central section and a wing formed onto an end of the central section, the wing projecting from the central section at an acute downward angle relative thereto; and
       (ii) a door adapted to be displaced between an open position and a closed position, the door comprising a layer of radiation shielding material, a front face, a rear face, a top face, a bottom face, a left-side face and a right-side face, the rear face of the door including a conductive portion;
       (iii) wherein, when in its closed position, the door encloses the passageway and the conductive portion on the rear face is adapted to selectively contact the frame through a continuous conductive seal;
    (c) a bracket connected to the door; and
    (d) at least one conductive gasket conductively coupled to the conductive portion on the rear surface of the door, wherein, with the door in its closed position, the at least one conductive gasket contacts the sill;
    (e) wherein the door assembly cooperates with the single enclosure to form an electromagnetic barrier around the room interior in all directions;
    (f) wherein the door assembly cooperates with the single enclosure to form a radiation barrier around the room interior in all directions.

11. The electromagnetic and radiation shielding system as claimed in claim 10 wherein the wing is adapted to project into a slot formed in the flooring in which the sill is mounted.

12. The electromagnetic and radiation shielding system as claimed in claim 11 wherein the gasket is adapted to project into the slot when the door is disposed in its open position.

* * * * *